US012677852B2

(12) United States Patent
Kaplan et al.

(10) Patent No.: US 12,677,852 B2
(45) Date of Patent: ***Jul. 14, 2026

(54) CULTURED TISSUE AND BIOREACTOR SYSTEMS AND METHODS FOR PRODUCTION THEREOF

(71) Applicant: Trustees of Tufts College, Medford, MA (US)

(72) Inventors: David L. Kaplan, Medford, MA (US); John Yuen, Medford, MA (US); Natalie R. Rubio, Medford, MA (US)

(73) Assignee: Trustees of Tufts College, Medford, MA (US)

( * ) Notice: Subject to any disclaimer, the term of this patent is extended or adjusted under 35 U.S.C. 154(b) by 671 days.

This patent is subject to a terminal disclaimer.

(21) Appl. No.: 18/041,363

(22) PCT Filed: Aug. 12, 2021

(86) PCT No.: PCT/US2021/071171
§ 371 (c)(1),
(2) Date: Feb. 10, 2023

(87) PCT Pub. No.: WO2022/036370
PCT Pub. Date: Feb. 17, 2022

(65) Prior Publication Data
US 2023/0284662 A1 Sep. 14, 2023

Related U.S. Application Data

(60) Provisional application No. 63/064,776, filed on Aug. 12, 2020.

(51) Int. Cl.
*A23L 13/00* (2016.01)
*C12M 1/00* (2006.01)
(Continued)

(52) U.S. Cl.
CPC ............. *A23L 13/00* (2016.08); *C12M 21/08* (2013.01); *C12M 23/58* (2013.01); *C12M 25/14* (2013.01);
(Continued)

(58) Field of Classification Search
CPC ....... A23L 13/00; C12M 21/08; C12M 23/58; C12M 25/14; C12M 29/16; C12N 5/0068;
(Continued)

(56) References Cited

U.S. PATENT DOCUMENTS

| | | |
|---|---|---|
| 6,902,932 B2 | 6/2005 | Altman et al. |
| 7,775,965 B2 | 8/2010 | McFetridge |

(Continued)

FOREIGN PATENT DOCUMENTS

| | | |
|---|---|---|
| CA | 2849987 C | 3/2023 |
| WO | 2005111193 A1 | 11/2005 |

(Continued)

OTHER PUBLICATIONS

Kaplan, David L., John Yuen, Natalie R. Rubio. U.S. Appl. No. 18/041,371. "Cultured Tissue and Bioreactor Systems and Methods for Production Thereof", filed Aug. 12, 2021 (Year: 2021).*

(Continued)

*Primary Examiner* — Michael L Hobbs
(74) *Attorney, Agent, or Firm* — Quarles & Brady LLP

(57) ABSTRACT

The present disclosure relates to cultured tissue, methods for production of the cultured tissue, and a bioreactor system for production of the cultured tissue. In some embodiments, the production of the cultured tissue may involve, at a first bioreactor, feeding a fiber scaffold into a chamber containing culture media, seeding the chamber with precursor cells, and allowing the precursor cells to proliferate and differentiate on a surface of the fiber scaffold. At downstream bioreactors, the production of the cultured tissue may further involve (Continued)

twisting a plurality of the cell-laden fibers to provide a cell-laden yarn, and weaving or knitting the cell-laden yarn into a three-dimensional (3D) structure. In some embodiments, the cultured tissue may be whole muscle cultured meat composed of muscle cell-laden fibers and fat cell-laden fibers. The whole muscle cultured meat may have a structural organization and hierarchy that mimics natural skeletal muscle tissue.

20 Claims, 6 Drawing Sheets

(51) Int. Cl.

| | |
|---|---|
| *C12M 1/12* | (2006.01) |
| *C12M 3/00* | (2006.01) |
| *C12N 5/00* | (2006.01) |
| *C12N 5/071* | (2010.01) |
| *C12N 5/077* | (2010.01) |

(52) U.S. Cl.
CPC ........... *C12M 29/16* (2013.01); *C12N 5/0068* (2013.01); *C12N 5/0658* (2013.01); *C12N 5/0697* (2013.01); *C12N 2513/00* (2013.01); *C12N 2533/50* (2013.01)

(58) Field of Classification Search
CPC .. C12N 5/0658; C12N 5/0697; C12N 5/0667; C12N 2513/00; C12N 2533/50; C12N 2537/00
See application file for complete search history.

(56) References Cited

U.S. PATENT DOCUMENTS

| | | | | |
|---|---|---|---|---|
| 9,456,893 | B2 | 10/2016 | Ling | |
| 11,319,866 | B1 * | 5/2022 | VanDerWege | F02M 23/00 |
| 12,325,866 | B2 * | 6/2025 | Nahmias | C12M 29/18 |
| 2003/0100108 | A1 | 5/2003 | Altman et al. | |
| 2003/0114061 | A1 | 6/2003 | Matsuda et al. | |
| 2004/0009600 | A1 | 1/2004 | Bowlin et al. | |
| 2005/0089552 | A1 | 4/2005 | Altman et al. | |
| 2005/0203636 | A1 | 9/2005 | McFetridge | |
| 2008/0009062 | A1 | 1/2008 | Bae et al. | |
| 2011/0076384 | A1 | 3/2011 | Cannizzaro et al. | |
| 2013/0030548 | A1 | 1/2013 | Ling | |
| 2013/0105348 | A1 | 5/2013 | Koob | |
| 2014/0234388 | A1 | 8/2014 | Christ et al. | |
| 2015/0359621 | A1 | 12/2015 | Sostek | |
| 2016/0067372 | A1 | 3/2016 | Davis et al. | |
| 2020/0140821 | A1 | 5/2020 | Elfenbein et al. | |

FOREIGN PATENT DOCUMENTS

| | | |
|---|---|---|
| WO | 2006068421 A1 | 6/2006 |
| WO | 2014110300 A1 | 7/2014 |
| WO | 2015061907 A1 | 5/2015 |
| WO | 2018227016 A1 | 12/2018 |

OTHER PUBLICATIONS

Extended European Search Report in European Application No. 21856892.1; received on Sep. 19, 2024.
Verbruggen, Sanne, et al. "Bovine myoblast cell production in a microcarriers-based system." Cytotechnology 70 (2018): 503-512.
Wang, Biqiao, et al. "Design and properties of a new braided poly lactic-co-glycolic acid catheter for peripheral nerve regeneration." Textile Research Journal 85.1 (2015): 51-61.
Wang, Mao, et al. "Mechanical properties of electrospun silk fibers." Macromolecules 37.18 (2004): 6856-6864.

Wang, Mao, et al. "Production of submicron diameter silk fibers under benign processing conditions by two-fluid electrospinning." Macromolecules 39.3 (2006): 1102-1107.
Wang, Xiaoqin, et al. "Silk coatings on PLGA and alginate microspheres for protein delivery." Biomaterials 28.28 (2007): 4161-4169.
Wittmer, Corinne R., et al. "Multifunctionalized electrospun silk fibers promote axon regeneration in the central nervous system." Advanced functional materials 21.22 (2011): 4232-4242.
Woerdeman, Dara L., et al. "Electrospun fibers from wheat protein: investigation of the interplay between molecular structure and the fluid dynamics of the electrospinning process." Biomacromolecules 6.2 (2005): 707-712.
Xu, Helan, et al. "Electrospun ultrafine fibrous wheat glutenin scaffolds with three-dimensionally random organization and water stability for soft tissue engineering." Journal of biotechnology 184 (2014): 179-186.
Yao, Chen, Xinsong Li, and Tangying Song. "Electrospinning and crosslinking of zein nanofiber mats." Journal of applied polymer science 103.1 (2007): 380-385.
Youngstrom, Daniel W., et al. "A bioreactor system for in vitro tendon differentiation and tendon tissue engineering." Journal of Orthopaedic Research 33.6 (2015): 911-918.
Zahari, Nor Kamalia, Ruszymah Binti Haji Idrus, and Shiplu Roy Chowdhury. "Laminin-coated poly (methyl methacrylate)(PMMA) nanofiber scaffold facilitates the enrichment of skeletal muscle myoblast population." International journal of molecular sciences 18.11 (2017): 2242.
Zhang, Guoqiang, et al. "Challenges and possibilities for biomanufacturing cultured meat." Trends in Food Science & Technology 97 (2020): 443-450.
Zhang, Menglin, et al. "Production of textile fibers from zein and a soy protein-zein blend." Cereal chemistry 74.5 (1997): 594-598.
Zhou, Wenda, et al. "Multifunctional bioreactor system for human intestine tissues." ACS Biomaterials Science & Engineering 4.1 (2018): 231-239.
International Search Report in PCT/US2021/071171; received on Nov. 4, 2021.
Ahn, Hyunchul, et al. "3D braid scaffolds for regeneration of articular cartilage." Journal of the Mechanical Behavior of Biomedical Materials 34 (2014): 37-46.
Akbari, Mohsen, et al. "Textile technologies and tissue engineering: a path toward organ weaving." Advanced healthcare materials 5.7 (2016): 751-766.
Altman, Gregory H., et al. "Silk-based biomaterials." Biomaterials 24.3 (2003): 401-416.
Altman, Gregory H., et al. "Silk matrix for tissue engineered anterior cruciate ligaments." Biomaterials 23.20 (2002): 4131-4141.
Altman, Gregory H., et al. "Helically organized silk fibroin fiber bundles for matrices in tissue engineering." U.S. Pat. No. 6,902,932. Jun. 7, 2005.
Balmaceda, Estela, and Chokyun Rha. "Spinning of zein." Journal of Food Science 39.2 (1974): 226-229.
Barber, John G., et al. "Braided nanofibrous scaffold for tendon and ligament tissue engineering." Tissue Engineering Part A 19.11-12 (2013): 1265-1274.
Bellas, Evangelia, et al. "In vitro 3D full-thickness skin-equivalent tissue model using silk and collagen biomaterials." Macromolecular bioscience 12.12 (2012): 1627-1636.
Ben-Arye, Tom, et al. "Textured soy protein scaffolds enable the generation of three-dimensional bovine skeletal muscle tissue for cell-based meat." Nature Food 1.4 (2020): 210-220.
Boublik, Jan, et al. "Mechanical properties and remodeling of hybrid cardiac constructs made from heart cells, fibrin, and biodegradable, elastomeric knitted fabric." Tissue Engineering 11.7-8 (2005): 1122-1132.
Castro, Guillermo R., et al. "Triggered release of proteins from emulsan-alginate beads." Journal of controlled release 109.1-3 (2005): 149-157.
Chen, Guoping, et al. "Culturing of skin fibroblasts in a thin PLGA-collagen hybrid mesh." Biomaterials 26.15 (2005): 2559-2566.
Chen, Jingsong, et al. "Human bone marrow stromal cell and ligament fibroblast responses on RGD-modified silk fibers." Journal

(56) References Cited

OTHER PUBLICATIONS of Biomedical Materials Research Part A: An Official Journal of The Society for Biomaterials, The Japanese Society for Biomaterials, and The Australian Society for Biomaterials and the Korean Society for Biomaterials 67.2 (2003): 559-570.

Desiderio, Vincenzo, et al. "Human Ng2+ adipose stem cells loaded in vivo on a new crosslinked hyaluronic acid-lys scaffold fabricate a skeletal muscle tissue." Journal of cellular physiology 228.8 (2013): 1762-1773.

Dinis, Tony M., et al. "Method to form a fiber/growth factor dual-gradient along electrospun silk for nerve regeneration." ACS applied materials & interfaces 6.19 (2014): 16817-16826.

Farvid, M. S., et al. "Association of adiponectin and resistin with adipose tissue compartments, insulin resistance and dyslipidaemia." Diabetes, obesity and metabolism 7.4 (2005): 406-413.

Fish, Kyle D., et al. "Prospects and challenges for cell-cultured fat as a novel food ingredient." Trends in food science & technology 98 (2020): 53-67.

Gong, Shengju, et al. "Mechanical properties and in vitro biocompatibility of porous zein scaffolds." Biomaterials 27.20 (2006): 3793-3799.

Hoh, Joseph FY, et al. "Three hierarchies in skeletal muscle fibre classification allotype, isotype and phenotype." NASA. Lyndon B. Johnson Space Center, Spacelab Life Sciences 1: Reprints of Background Life Sciences Publications (1991).

Huang, H. C., et al. "Properties of fibers produced from soy protein isolate by extrusion and wet-spinning." Journal of the American Oil Chemists' Society 72.12 (1995): 1453-1460.

Ikada, Yoshito. "Challenges in tissue engineering." Journal of the Royal Society Interface 3.10 (2006): 589-601.

Kinahan, Michelle E., et al. "Tunable silk: using microfluidics to fabricate silk fibers with controllable properties." Biomacromolecules 12.5 (2011): 1504-1511.

Kong, Lingyan, and Gregory R. Ziegler. "Fabrication of pure starch fibers by electrospinning." Food Hydrocolloids 36 (2014): 20-25.

Rubio, Natalie, et al. "Cell-based fish: a novel approach to seafood production and an opportunity for cellular agriculture." Frontiers in Sustainable Food Systems 3 (2019): 43.

Kuthe, Chetan D., R. V. Uddanwadiker, and Alankar Ramteke. "Experimental evaluation of fiber orientation based material properties of skeletal muscle in tension." Molecular & Cellular Biomechanics 11.2 (2014): 113.

Liao, I-Chien, et al. "Composite three-dimensional woven scaffolds with interpenetrating network hydrogels to create functional synthetic articular cartilage." Advanced functional materials 23.47 (2013): 5833-5839.

Lovett, Michael, et al. "Simple modular bioreactors for tissue engineering: a system for characterization of oxygen gradients, human mesenchymal stem cell differentiation, and prevascularization." Tissue Engineering Part C: Methods 16.6 (2010): 1565-1573.

Lu, Ming-Chin, et al. "Evaluation of a multi-layer microbraided polylactic acid fiber-reinforced conduit for peripheral nerve regeneration." Journal of Materials Science: Materials in Medicine 20 (2009): 1175-1180.

Lutolf, Matthias P., and J. A. Hubbell. "Synthetic biomaterials as instructive extracellular microenvironments for morphogenesis in tissue engineering." Nature biotechnology 23.1 (2005): 47-55.

Marano, RP Casaroli, and Senen Vilaro. "The role of fibronectin, laminin, vitronectin and their receptors on cellular adhesion in proliferative vitreoretinopathy." Investigative ophthalmology & visual science 35.6 (1994): 2791-2803.

Marolt, Darja, et al. "Bone and cartilage tissue constructs grown using human bone marrow stromal cells, silk scaffolds and rotating bioreactors." Biomaterials 27.36 (2006): 6138-6149.

Martins, Albino, et al. "Hierarchical starch-based fibrous scaffold for bone tissue engineering applications." Journal of tissue engineering and regenerative medicine 3.1 (2009): 37-42.

Mayer, Jean M., et al. "Biodegradable blends of cellulose acetate and starch: production and properties." Journal of Macromolecular Science, Part A: Pure and Applied Chemistry 32.4 (1995): 775-785.

Müller, Frank A., et al. "Cellulose-based scaffold materials for cartilage tissue engineering." Biomaterials 27.21 (2006): 3955-3963.

Ng, Kee Woei, and Dietmar Werner Hutmacher. "Reduced contraction of skin equivalent engineered using cell sheets cultured in 3D matrices." Biomaterials 27.26 (2006): 4591-4598.

Ohkawa, Kousaku, et al. "Electrospinning of chitosan." Macromolecular rapid communications 25.18 (2004): 1600-1605.

Onoe, Hiroaki, et al. "Metre-long cell-laden microfibres exhibit tissue morphologies and functions." Nature materials 12.6 (2013): 584-590.

Ozgen, Banu. "New biodegradable fibres, yarn properties and their applications in textiles: a review." Industria Textile 63 (2012): 3-6.

Pedde, R. Daniel, et al. "Emerging biofabrication strategies for engineering complex tissue constructs." Advanced Materials 29.19 (2017): 1606061.

Simmons, S., et al. "Thermoplastic processing of starch: melt-spinning of starch-based fibers." Biodegradable Polymer Packaging (1993): 171-207.

Siriwardane, Mevan L., et al. "Controlled formation of cross-linked collagen fibers for neural tissue engineering applications." Biofabrication 6.1 (2014): 015012.

Sokolnicki, Adam M., et al. "Permeability of bacterial cellulose membranes." Journal of membrane science 272.1-2 (2006): 15-27.

Tiğli R. Seda, et al. "Chondrogenesis in perfusion bioreactors using porous silk scaffolds and hESC-derived MSCs." Journal of Biomedical Materials Research Part A 96.1 (2011): 21-28.

Tuzlakoglu, Kadriye, et al. "Production and characterization of chitosan fibers and 3-D fiber mesh scaffolds for tissue engineering applications." Macromolecular Bioscience 4.8 (2004): 811-819.

Tuzlakoglu, Kadriye, et al. "A new route to produce starch-based fiber mesh scaffolds by wet spinning and subsequent surface modification as a way to improve cell attachment and proliferation." Journal of Biomedical Materials Research Part A: An Official Journal of The Society for Biomaterials, The Japanese Society for Biomaterials, and The Australian Society for Biomaterials and the Korean Society for Biomaterials 92.1 (2010): 369-377.

Urbanchek, Melanie G., et al. "Specific force deficit in skeletal muscles of old rats is partially explained by the existence of denervated muscle fibers." The Journals of Gerontology Series A: Biological Sciences and Medical Sciences 56.5 (2001): B191-B197.

Van der Weele, Cor, and Johannes Tramper. "Cultured meat: every village its own factory?. " Trends in biotechnology 32.6 (2014): 294-296.

Vaquette, Cedryck, et al. "Aligned poly (L-lactic-co-e-caprolactone) electrospun microfibers and knitted structure: a novel composite scaffold for ligament tissue engineering." Journal of Biomedical Materials Research Part A 94.4 (2010): 1270-1282.

Vega-Lugo, Ana-Cristina, and Loong-Tak Lim. "Electrospinning of soy protein isolate nanofibers." Journal of Biobased Materials and Bioenergy 2.3 (2008): 223-230.

* cited by examiner

Feed fiber scaffold into chamber — 32

Seed chamber with precursor cells — 36

Allow precursor cells to proliferate/differentiate on surface of fiber scaffold — 38

Twist cell-laden fibers to provide a cell-laden fiber yarn — 40

Weave or knit cell-laden fiber yarn into 2D/3D structure — 42

12

CULTURED TISSUE AND BIOREACTOR SYSTEMS AND METHODS FOR PRODUCTION THEREOF

CROSS-REFERENCE TO RELATED APPLICATIONS

This application is the national stage entry of PCT/US2021/071171, filed Aug. 12, 2021 which is related to, claims priority to, and incorporates herein by reference for all purposes U.S. Provisional Patent Application No. 63/064,776, filed Aug. 12, 2020. The contents of these applications are incorporated by reference herein.

BACKGROUND

The present disclosure generally relates to cultured tissue and to methods for producing cultured tissue. The present disclosure further relates to bioreactor systems for manufacturing the cultured tissue. The cultured tissue may be cultured meat that resembles whole muscle meat.

Conventional animal agriculture for the production of meat (muscle and fat tissue) is linked to numerous drawbacks such as environmental degradation, zoonic disease emergence, antimicrobial resistance, and animal welfare concerns. As meat production is predicted to increase over the coming decades, the impact of meat production and consumption on human health and the environment is expected to increase as well. To reduce these negative impacts on animals and the environment, there is increasing interest in producing alternatives to conventional animal meat. In order to satisfy the same consumer demand that drives meat consumption, it is desirable that these alternatives to conventional animal meat be comparable in terms of taste, texture, and sensory properties. Plant based meat utilizes plant or other non-animal components to mimic animal meat, and bypasses the low efficiency feed to food conversion ratios encountered when raising livestock for meat.

Cultured meat (also called in vitro, cultivated, lab grown meat) prepared using tissue and bioengineering techniques in vitro is another alternative to traditional animal agriculture. By directly growing meat (muscle and fat tissue) in vitro, energy and nutrients may be more efficiently focused on the outcome. The time frame to generate cultured meat tissues in vitro is also thought to be faster compared to traditional animal agriculture, and may only require weeks as opposed to months or years for pork and beef, for example. Moreover, tight control over cell biology during tissue cultivation, as well as the production process, allows for the fine tuning of nutritional parameters by engineering muscle or fat cells to produce vital nutrients that would otherwise not be found (or found only at low concentrations) in conventional meat. Thus, cultured meat production systems may offer healthier, more efficient, and more environmentally friendly alternatives to animal-derived meats.

With the advent of tissue engineering for the production non-animal derived foods, a particular challenge is not only cell and tissue density, but also the alignment of the cells and matrices (scaffolds, extracellular matrix) to emulate the native structure and function of tissues and food. For example, achieving mechanical requirements as well as mastication and organoleptic features are important goals. In vivo, animal skeletal muscles are striated and packed into dense arrangements of fiber bundles. In meat, these features provide the specific texture and mouthfeel obtained when biting into a whole muscle cut of meat (e.g., steak). Current bioreactors for cultured meat production focus on increasing cell density (via increased surface area with internal plates or suspension particles) and optimizing nutrient flow (e.g., oxygen, glucose), with less focus on mimicking the texture and structural hierarchy of mammalian muscle tissue. However, for future needs in manufacturing for meat-like foods, tissue density and structural organization are key outcomes for food texture, nutrient density, and consumer acceptance.

Another limitation of cultured meat is scalability. Small-scale production increases the price of cultured meat alternatives, making such products prohibitively expensive for many consumers. Scalable, replicable, and automated processes for cultured meat production are needed before cultured meat can become a viable alternative for consumers.

Thus, there remains a need for systems and methods that enable the large-scale production of cultured meat/muscle tissues with structural attributes that mimic native skeletal muscle. The present disclosure provides a technical solution for these needs.

SUMMARY

Disclosed herein is a system for the production of cultured tissue. The system may include a first bioreactor. The first bioreactor may include an internal chamber containing culture medium, a fiber inlet for feeding a fiber scaffold into the internal chamber, and a cell inlet for feeding precursor cells into the internal chamber. The precursor cells may proliferate and differentiate on a surface of the fiber scaffold in the culture medium to provide a cell-laden fiber composed of cells attached to the fiber scaffold. The first bioreactor may further include an outlet through which the cell-laden fiber emerges from the first bioreactor. The cell-laden fiber may be used in the production of the cultured tissue.

Further disclosed herein is a method for producing cultured tissue. The method may include feeding a fiber scaffold into a chamber containing culture medium, seeding the chamber with precursor cells, and allowing the precursor cells to proliferate and differentiate on a surface of the fiber scaffold to provide a cell-laden fiber composed of cells adhered to the fiber scaffold. The method may further include twisting a plurality of cell-laden fibers to provide a cell-laden yarn, and weaving or knitting the cell-laden yarn into a three-dimensional (3D) structure to provide the cultured tissue.

Also disclosed herein is cultured tissue including a plurality of cell-laden fibers each comprised of cells attached to a fiber scaffold. The plurality of cell-laden fibers may be twisted into a cell-laden yarn, and the cell-laden yarn may be further woven or knitted into a three-dimensional (3D) shape. The cultured tissue may exhibit a structural organization that mimics skeletal muscle tissue.

DETAILED DESCRIPTION

Before the present invention is described in further detail, it is to be understood that the invention is not limited to the particular embodiments described. It is also understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. When two or more ranges for a particular value are recited, this disclosure contemplates all combinations of the upper and lower bounds of those ranges that are not explicitly recited. For example, recitation of a value of between 1 and 10 or between 2 and 9 also contemplates a value of between 1 and 9 or between 2 and 10.

Figure 1:
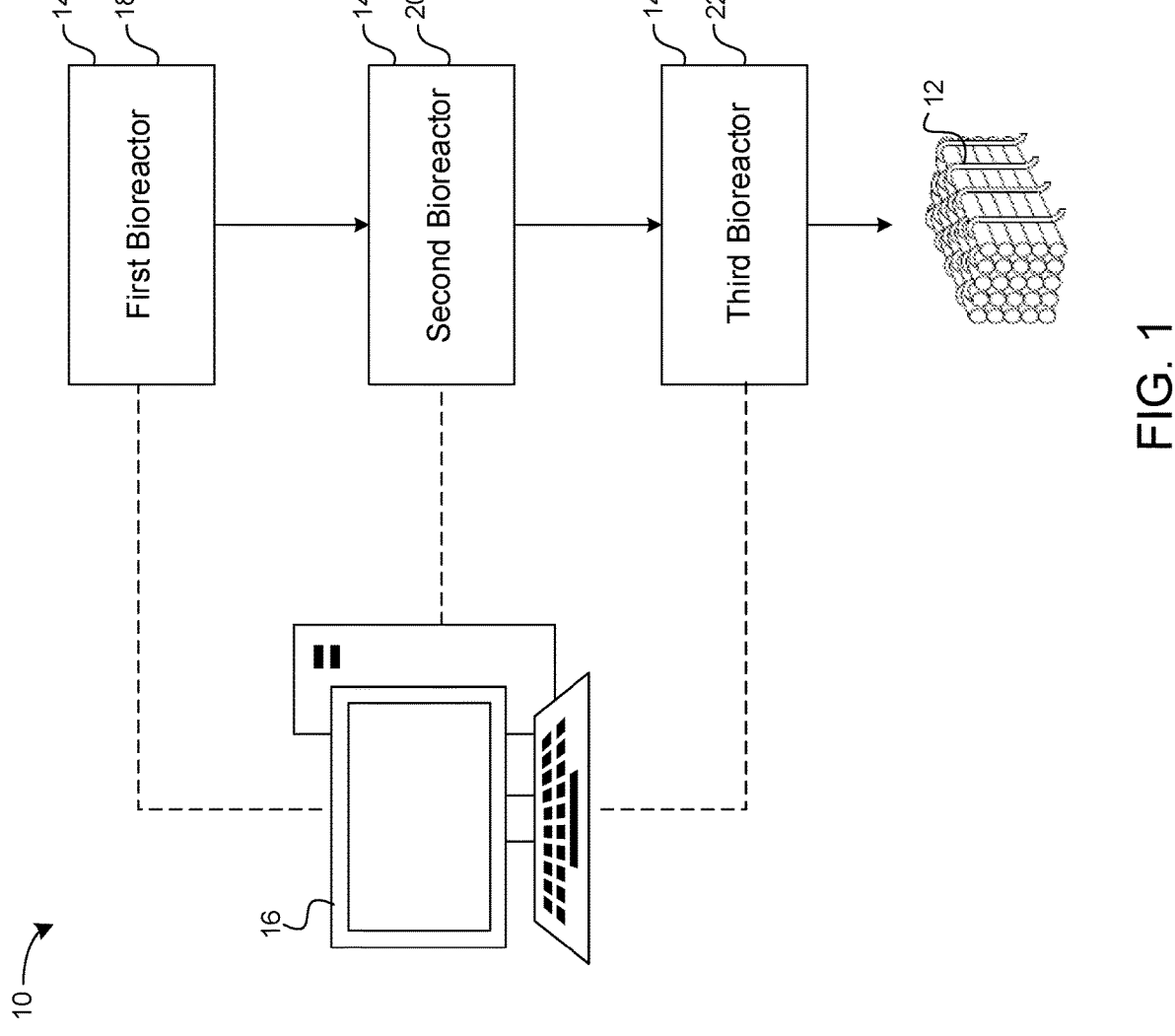
FIG. 1 is a schematic representation of a system for the production of cultured tissue, according to an embodiment of the present disclosure.

Referring to the drawings, and with specific reference to FIG. 1, a system 10 for the large-scale production of cultured tissue 12 is shown. The cultured tissue 12 may be cultured whole muscle meat suitable for consumption and having a structural organization and hierarchy that mimics natural whole muscle meat. The system 10 employs principles from textile engineering to generate the cultured tissue 12, whereby fibers of muscle and fat are first cultured in vitro and then twisted into yarns and knitted/weaved and folded or stacked into large, macroscale two-dimensional (2D) or three-dimensional (3D) tissue constructs. This process imparts strength in the resulting cultured tissue 12 and provides a structural organization and hierarchy reminiscent of that in skeletal muscle tissue. In some embodiments, the cultured tissue 12 may have a stiffness that approaches, matches, or surpasses that of native bovine muscle (about 12 kilopascals (kPa)). The cultured tissue 12 may further exhibit marbling of fat tissue that resembles fat marbling in whole muscle meat. Although the cultured tissue 12 has a rectangular prism structure in FIG. 1 for simplicity, it will be understood that the cultured tissue 12 may have many other 2D or 3D shapes in practice.

The system 10 may include one or more bioreactors 14 or bioreactor stations which operate to produce the cultured tissue 12. The system 10 may be run in separate unit operations, or as a continuous, robotically-controlled, and automated process. For the continuous, automatic process, the output from each stage/bioreactor 14 may be fed directly into the next, allowing for minimal human intervention, sterility, and reduced risk of cell contamination. One or more computer controllers 16 may be in communication with the bioreactors 14 for automating and controlling the operations thereof. In some embodiments, the system 10 may include a first bioreactor 18, a second bioreactor 20 downstream of the first bioreactor 18, and a third bioreactor 22 downstream of the second bioreactor 20.

Figure 3:
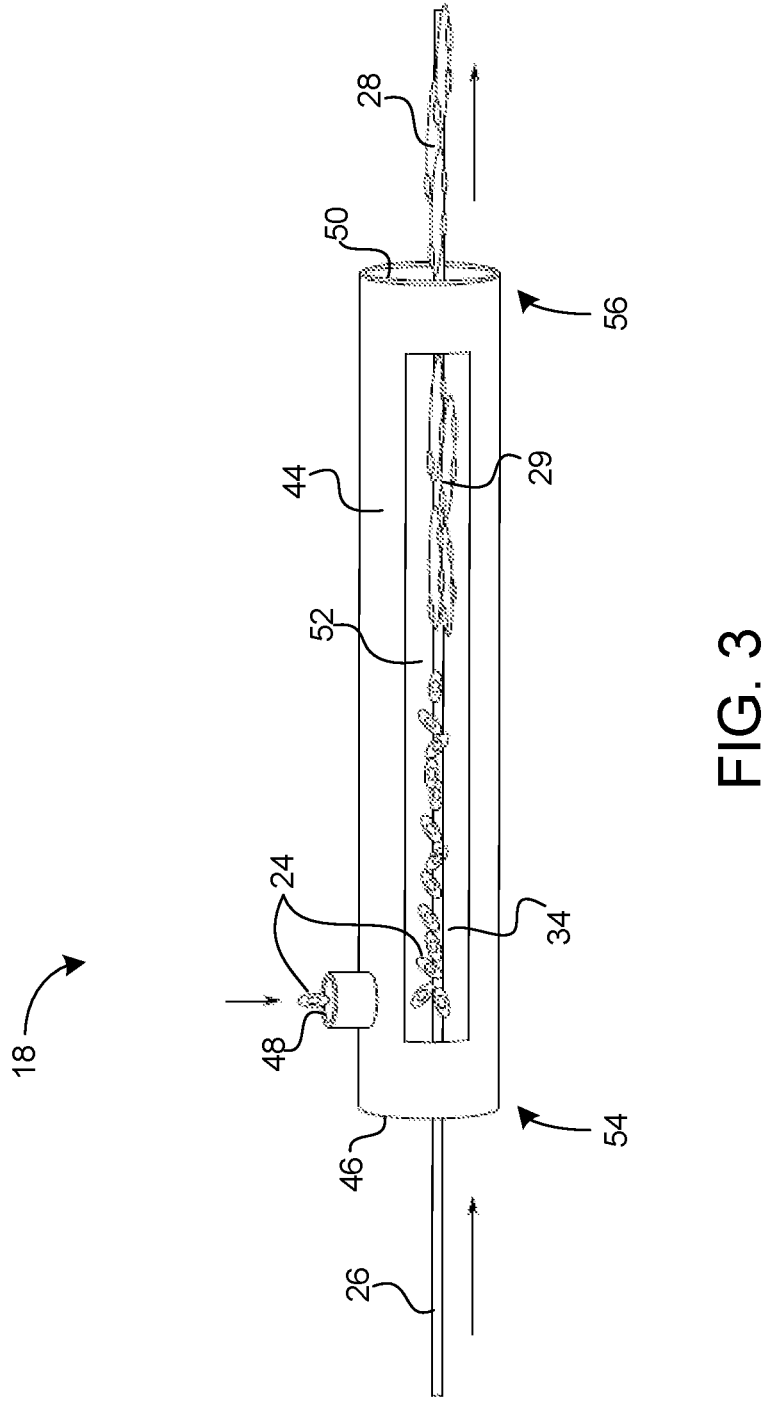
FIG. 3 is a schematic representation of a first bioreactor of the system of FIG. 1, according to an embodiment of the present disclosure.

In the first bioreactor 18, precursor cells 24 (e.g., satellite cells, adipogenic precursor cells) may proliferate and differentiate on a fiber scaffold 26 in culture media to provide a cell-laden fiber 28 composed of mature cells 29 (mature muscle or fat cells) attached to the fiber scaffold 26 (also see FIG. 3). The fiber scaffold 26 may be composed of a fiber. As used herein, a "fiber" is a basic building block of a fabric that is significantly longer than it is wide. A plurality of the cell-laden fibers 28 emerging from one or more of the first bioreactors 18 may be combined and twisted to form a cell-laden yarn 30 at the second bioreactor 20 (also see FIG. 4). As used herein, a "yarn" is a continuous strand of fibers that are spun or twisted together. The cell-laden yarn 30 emerging from the second bioreactor 20 may be knitted or woven and folded, rolled, and/or stacked into various 2D and 3D constructs at the third bioreactor 22 (also see FIG. 5).

Inputs into the first bioreactor 18 may include the fiber scaffold 26, the precursor cells 24, and culture medium, and the output of the first bioreactor 18 may be the cell-laden fiber 28 (also see FIG. 3). The input and the output of the second bioreactor 20 may be cell-laden fibers 28 and the cell-laden yarn 30, respectively (also see FIG. 4). The input and the output of the third bioreactor 22 may include cell-laden fiber yarns 30 and the cultured tissue 12, respectively. In alternative embodiments, more or fewer bioreactors 14 may be used for the production of the cultured tissue 12, with the above operations of the bioreactors 14 delegated in various different ways.

Figure 2:
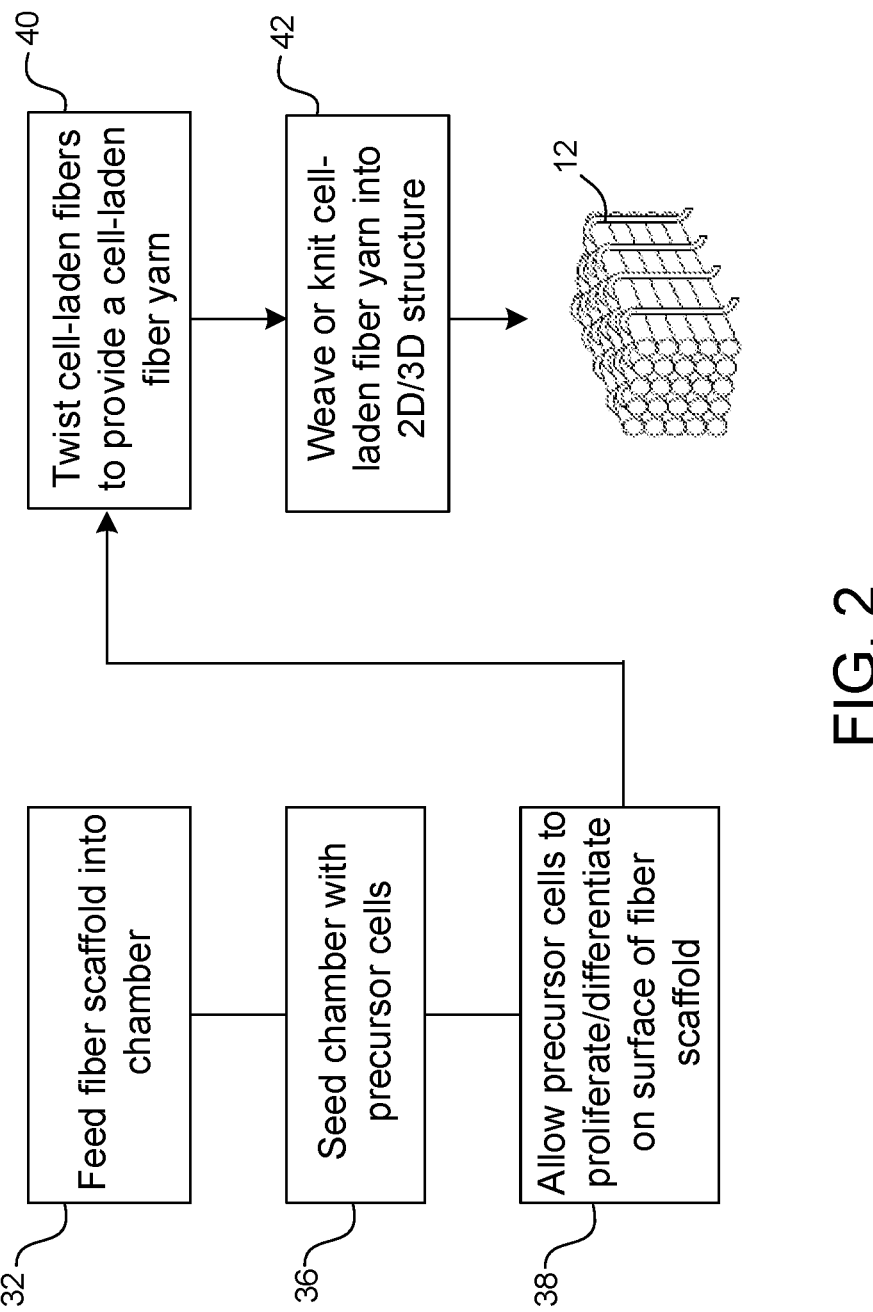
FIG. 2 is a flow chart of steps that may be involved in producing the cultured tissue, according to an embodiment of the present disclosure.

Turning to FIG. 2, a method for producing the cultured tissue 12 is shown. At a block 32, the fiber scaffold 26 may be fed into an internal chamber 34 of the first bioreactor 18 containing a culture medium (also see FIG. 3). A block 36 may involve seeding the internal chamber 34 containing the culture medium with precursor cells 24 (also see FIG. 3). The precursor cells 24 may be seeded onto the fiber scaffold 26 using a sol-gel dispensing system. The blocks 32 and 36 may be carried out in different orders or simultaneously in practice. At a following block 38, the precursor cells 24 may be permitted to proliferate and differentiate on a surface of the fiber scaffold 26 in the culture medium to provide the cell-laden fiber 28. The transit time and culture medium in the first bioreactor 18 may be tuned to provide a desired degree of coverage of differentiated cells on the fiber scaffold 26. In some embodiments, confluence (or a desired degree of coverage of differentiated cells on the surface of the fiber scaffold 26) may be identified when at least 70-80% of a surface area of the fiber scaffold 26 is coated with the mature cells. For example, the cells 24 may be cultured to a confluence of at least 75% surface area coverage in the first bioreactor 18. Cell differentiation may be indicated by the expression of myosin heavy chain (WIC) in muscle cells, and by the accumulation of lipid in fat cells.

At a next block 40, a plurality of cell-laden fibers 28 emerging from first bioreactors 18 may be combined and twisted to impart densification into the fiber-cell matrices and provide the cell-laden yarn 30. At a block 42, the cell-laden yarn 30 emerging from the second bioreactor 20 may be knitted or woven and folded or stacked into various 2D or 3D structures to provide the culture tissue 12. As explained above, the block 40 may be performed at the second bioreactor 20, and the block 42 may be performed at the third bioreactor 22.

As shown in FIG. 3, the first bioreactor 18 may include a body 44 having the internal chamber 34 containing the culture medium, one or more fiber inlets 46 for feeding the fiber scaffold 26 into the internal chamber 34, and one or more cell inlets 48 for feeding the precursor cells 24 into the internal chamber 34. In some aspects, the fiber scaffold 26 and the precursor cells 24 may be fed into the first bioreactor 18 via the same inlet. The first bioreactor 18 may further include one or more outlets 50 through which the cell-laden fiber 28 emerges from the first bioreactor 18. As the fiber scaffold 26 translates from the fiber inlet 46 to the outlet 50, the precursor cells 24 may attach to and proliferate on the surface of the fiber scaffold 26, and differentiate into mature cells 29 on the surface of the fiber scaffold 26. Different bioreactors (fiber scaffold lines) may be used for different cell types (muscle cells and fat cells) with appropriate media conditions for each. The fiber scaffold lines with different cell types may be combined in later stages of the process with continuous cultivation for expansion and differentiation with sufficient residence time in the system to optimize tissue outcomes (e.g., myotubes for muscle, fat droplets for fat, extracellular matrix depositions representative of those found in meat).

In some aspects, a time for the cells 24 to attach to and reach confluence on the fiber scaffold 26 may range from 12 to 48 hours, and a time for cell differentiation into the mature cells 29 may range from 7 to 21 days. In some embodiments, cell growth may be continued until a surface of the fiber scaffold 26 is at least 70% or at least 80% covered by differentiated cells. In some embodiments, cell differentiation of at least 90% may be achieved in the first bioreactor 18. Cell growth may continue once the cell-laden yarns 30 are woven into their desired forms, and may be halted by freezing during storage/transport. It may not be necessary for the cells to be alive once the fibers are formed, as the cultured tissue may be cooked prior to consumption.

Factors such as, but not limited to, the rate of translation of the fiber scaffold 26 through the first bioreactor 18 and the composition of the culture medium may be tuned/adjusted to provide a desired level of cell coverage or confluence on the fiber scaffold 26 and/or to control cell differentiation. For example, cell proliferation to differentiation may be driven by a shift in media composition. As a non-limiting example, satellite cells may be proliferated in a growth factor-rich proliferation media, and triggered for differentiation in a growth factor-poor differentiation media, with the concentration of the growth factor decreasing along the length of the internal chamber 34 from a proximal end 54 to a distal end 56.

Performing cell proliferation and differentiation initially on the fiber scaffold 26 at the first bioreactor 18 addresses mass transport issues of tissue engineering, as tissue densification (and its associated nutrient/$O_2$ diffusion constraints) is decoupled/delayed until after maturation of individual cell-laden fibers 28. Further, the use of cell-laden fibers 28 as the cultured meat building blocks fosters cell and extracellular matrix alignment along the fiber axis, thereby enhancing mechanics and texture.

Figure 4:
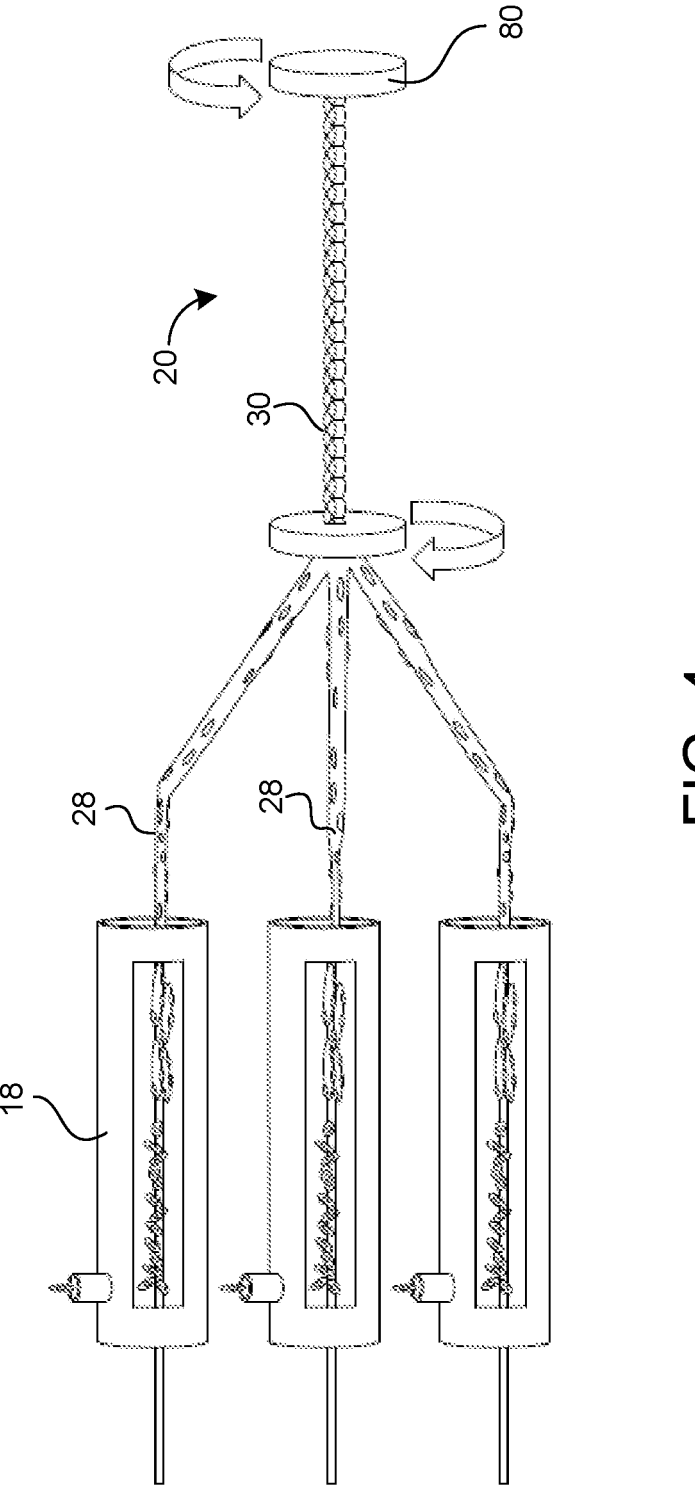
FIG. 4 is a schematic representation of an operation at a second bioreactor of the system of FIG. 1, according to an embodiment of the present disclosure.

A schematic representation of the second bioreactor 20 is shown in FIG. 4. The cell-laden fibers 28 emerging from one or more first bioreactors 18 may be transferred to the second bioreactor 20 for densification. Versatility in the resulting cell-laden yarn 30 may be provided by varying which process lines are combined at the second bioreactor 20. For instance, cell-laden yarns 30 composed of muscle cells, fat cells, and combinations thereof may be generated at the second bioreactor 20 by combining/twisting various combinations of muscle cell-laden fibers and fat cell-laden fibers. Twisting and/or braiding of the cell-laden fibers 28 using programmable strain rates and extents at the second bioreactor 20 may impart controlled densification into the resulting cell-laden yarn 30. The second bioreactor 20 may include wheels 80 driven by motors which attach to each end of the cell-laden fibers 28. The wheels 80 may rotate at a rotation rate to provide fiber bundles or yarns. The degree of twisting, yarn diameter, and yarn density may be determined based on combinations of mechanical targets (e.g., food-like for meats) and desired cell outcomes (e.g., survival, function, retention). The second bioreactor 20 may produce muscle cell-laden yarns with controlled densification that mimic the density of mammalian skeletal tissue (about 1.06 kilograms (kg)/liter (L), and fat cell-laden yarns with a density similar to adipose tissue (about 0.92 kg/L). The resulting yarns may have varying diameters. In some embodiments, the densified cell-laden yarns 30 emerging from the second bioreactor 20 may have diameters that range from about 50 micrometers (μm) to about 100 μm.

Figure 5:
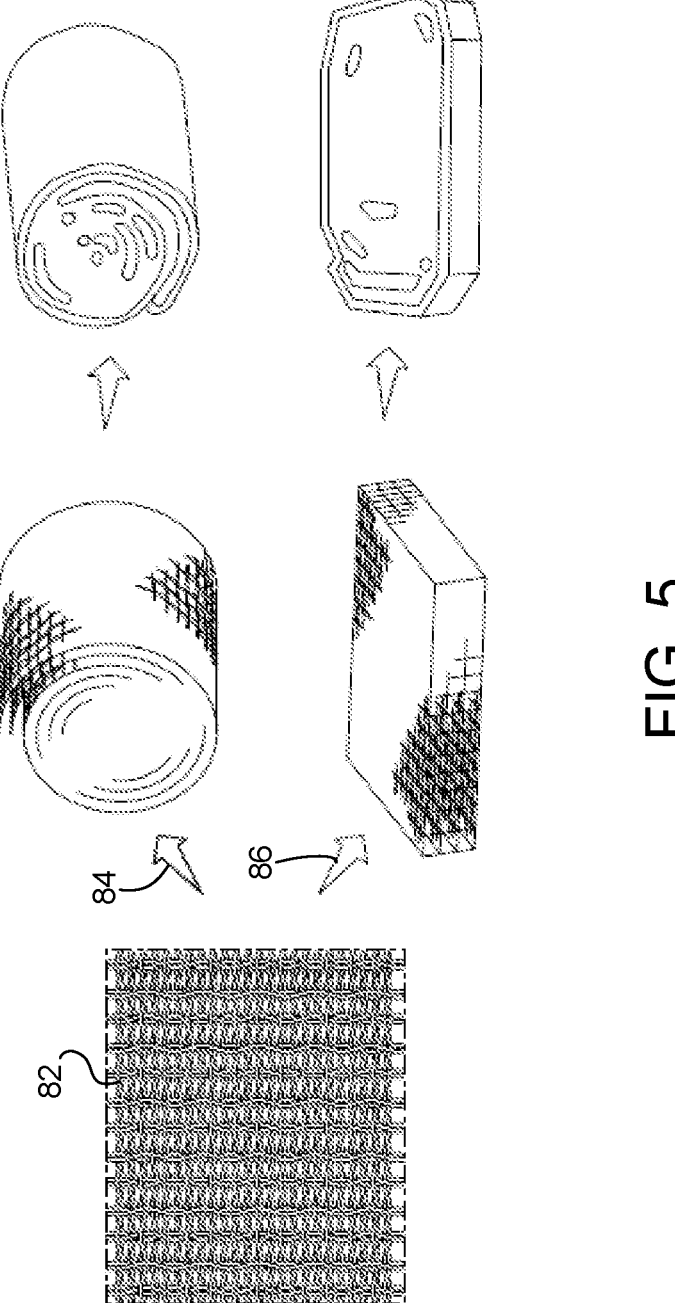
FIG. 5 is a schematic representation of operations performed at a third bioreactor of the system of FIG. 1, according to an embodiment of the present disclosure.

One or more of the densified cell-laden yarns 30 from the second bioreactor 20 may proceed to the weaving and knitting phase at the third bioreactor 22 which may build up 2D or 3D structures from the previously constructed muscle and adipose yarns. The inputs into the third bioreactor may include one or more muscle cell-laden yarns, one or more fat cell-laden yarns, or combinations of muscle cell-laden yarns and fat cell-laden yarns. The ratio of the muscle cell-laden yarns to the fat cell-laden yarns may be selected/controlled to provide various muscle and fat contents in the resulting cultured tissue 12, as well as to mimic marbling in whole muscle meat. As shown in FIG. 5, the cell-laden yarns 30 may be woven, braided, or knitted into 2D sheets 82, and one or more of the 2D sheets 82 may be folded, twisted, rolled 84, and/or stacked 86 to provide the 3D construct of the cultured tissue 12. The resulting cultured tissue 12 may emulate steak or meat rolls, for example. Alternatively, the cell-laden yarns 30 may be directly knitted or weaved into a 3D structure.

The fiber scaffold 26 may be made of an edible biomaterial that supports cell and tissue growth and is compatible for continuous culture in a flow through device. The fiber scaffold 26 may be composed of edible fibers from natural sources such as collagen, silk, and chitosan which have used in textile-based engineering. In addition to these materials, other edible and economic biomaterials such as wheat gluten, cellulose, zein, starch, fungal mycelia, and soy may also be used. Fabrication of these materials into fibers may be achieved by electrospinning (see, for example, Woerdeman, D. L.; Ye, P.; Shenoy, S.; Parnas, R. S.; Wnek, G. E.; Trofimova, O., Electrospun fibers from wheat protein: investigation of the interplay between molecular structure and the fluid dynamics of the electrospinning process, *Biomacromolecules* 2005, 6 (2), 707-712; Yao, C.; Li, X.; Song, T., Electrospinning and crosslinking of zein nanofiber mats, *Journal of applied polymer science* 2007, 103 (1), 380-385; Ohkawa, K.; Cha, D.; Kim, H.; Nishida, A.; Yamamoto, H., Electrospinning of chitosan, *Macromolecular rapid communications* 2004, 25 (18), 1600-1605; and Kong, L.; Ziegler, G. R., Fabrication of pure starch fibers by electrospinning.

7

*Food Hydrocolloids* 2014, 36, 20-25; Vega-Lugo, A.-C.; Lim, L.-T., Electrospinning of soy protein isolate nanofibers, *Journal of Biobased Materials and Bioenergy* 2008, 2 (3), 223-230—each of which is incorporated herein by reference in its entirety), wetspinning (see, for example, Tuzlakoglu, K.; Pashkuleva, I.; Rodrigues, M. T.; Gomes, M. E.; van Lenthe, G. H.; Müller, R.; Reis, R., A new route to produce starch-based fiber mesh scaffolds by wet spinning and subsequent surface modification as a way to improve cell attachment and proliferation, *Journal of Biomedical Materials Research Part A: An Official Journal of The Society for Biomaterials, The Japanese Society for Biomaterials, and The Australian Society for Biomaterials and the Korean Society for Biomaterials* 2010, 92 (1), 369-377; Huang, H.; Hammond, E.; Reitmeier, C.; Myers, D., Properties of fibers produced from soy protein isolate by extrusion and wet-spinning, *Journal of the American Oil Chemists' Society* 1995, 72 (12), 1453-1460; and Zhang, M.; Reitmeier, C. A.; Hammond, E. G.; Myers, D. J., Production of textile fibers from zein and a soy Protein-Zein blend. *Cereal chemistry* 1997, 74 (5), 594-598—each of which is incorporated herein by reference in its entirety), and meltspinning (see, for example, Balmaceda, E.; RHA, C., Spinning of zein. *Journal of Food Science* 1974, 39 (2), 226-229; Özgen, B., New biodegradable fibres, yarn properties and their applications in textiles: a review. *Industria Textile* 2012, 63, 3-6; and Simmons, S. In *Thermoplastic Processing of Starch: Melt-Spinning of Starch—Based Fibers, Biodegradable Polymer Packaging* (1993), Conference Proceedings, Publisher: Technomic, Lancaster, PA, pp 171-207—each of which is incorporated herein by reference in its entirety). Fibrous materials from natural sources may be used to foster cell expansion and tissue alignment, and to support cell differentiation on the fibers. The fiber materials may be commercially available as large-scale agricultural products and byproducts.

In some embodiments, the fiber scaffold 26 may support cell viability at greater than 80%, and cell adhesion at greater than 70% after 48 hours of culture with a differentiation efficiency within 20% of control (i.e., tissue culture plastic) conditions. In some aspects, the fiber scaffold 26 may support more than 90% cell coverage within 48 hours of culture when using a high cell seeding density. Furthermore, the fiber scaffold 26 may be strong enough to be handled and loaded between bioreactor components in the bioreactors without breaking or deforming. The fiber scaffold 26 may also be windable during operations. In some embodiments, the fiber scaffold 26 may have an ultimate tensile strength that ranges from 3 kilopascals (kPa) to 40 kPa. Additionally, the fiber scaffold 26 may conform to the mechanical properties of meats with Warner Bratzler Shear force values of 2 to 8 kg, thus capturing the required strength for textile engineering as well as consumer expectations in terms of bite and chew. These properties may be attributes of the fiber scaffold 26 alone or with one or more coatings.

The fiber scaffold 26 may include one or more coatings to provide desirable properties such as those mentioned above, and/or to improve cell attachment to the fiber scaffold 26. Various cost-effective biopolymers or complex extracts from natural sources may be used as coating materials. In some embodiments, extracellular matrix proteins and/or chemical/synthetic coatings may be used as coatings to improve cell attachment to the natural fibers and mimic in vivo cell behavior. Other types of coating materials may include commercially available products such as, but not limited to, fibronectin, laminin, vitronectin, collagen, cadherin, elastin, hyaluronic acid, poly-D-lysine, poly-L-lysine, poly-L-ornithine, concanavalin A, and other adhesive, non-toxic chemicals. Conconavalin A, laminin, and hyaluronic acid may be obtained from animal-free origins, and have been shown to enhance muscle cell attachment to various biomaterials. The fiber scaffold 26 may have a gel coating.

The cells 29 may be edible cells including muscle cells, fat cells, and combinations thereof. The precursor cells 24 may be muscle precursor cells or adipoctye precursor cells. Examples of suitable cell types include, but are not limited to, satellite cells, fat cells (i.e., adipocytes), fibroblasts, myoblasts, muscle cells, precursors thereof, and combinations thereof. The cells may be from animal source including, without limitation, from bovine, avian (e.g., chicken, quail), porcine, or murine sources. The cells may also be derived from seafood such as fish (e.g., salmon, tuna, etc.), shellfish (e.g., clams, mussels, and oysters); crustaceans (e.g., lobsters, shrimp, prawns, and crayfish), and echinoderms (e.g., sea urchins and sea cucumbers). In some embodiments, the cells 29 may be engineered to produce vital nutrients such as proteins and essential fatty acids. In addition, transgenic cells may be used to decrease the time needed for cell differentiation. In some aspects, media formulations may include transgenic components to drive cell differentiation. For example, tetracycline-responsive promoters inserted into transgenic cells may be activated by including tetracycline in the culture medium, resulting in forced expression of myogenic or adipogenic genes in edible cell lines (e.g., chicken fibroblasts, bovine satellite cells, etc.).

Cells (e.g., muscle, fat) may be seeded onto fibers using a sol-gel dispensing system with separate fiber/yarn lines for the two cell types and appropriate media conditions for each. In one embodiment, bovine satellite cells may be continuously seeded onto the fiber scaffold (with or without coatings). Bovine satellite cells may be cultured in growth media with growth factors (e.g., DMEM with Glutamax, 20% FBS, and 1% antiobiotic-antimycotic, and 1 ng/mL human fibroblast growth factor 2 (FGF-2)). To differentiate satellite cells into mature myotubes, cells may be cultured to confluence and triggered for differentiation by a low growth factor environment. For example, the culture medium may shift from a growth factor-rich proliferation media to a growth factor-poor differentiation media.

Bovine fat cells may also be coated onto the fiber scaffold 26 and cultured in growth media (e.g., DMEM with Glutamax, 20% FBS, 1% antibiotic-antimycotic). To differentiate adipogenic precursor cells into mature adipocytes, cells may be cultured to a desired confluence (e.g., 75%), and the media may then be supplemented with free fatty acid solution. An exemplary free fatty acid solution may be 50 millimolar (mM) free fatty acid solutions containing elaidic acid, erucic acid, myristoleic acid, oleic acid, palmitoleic acid, phytanic acid, and pristanic acid. To verify lipid accumulation, Oil Red 0 (ORO) may be used to stain differentiated cells.

Various parameters of the system 10 may be controlled/programmed via the computer controller 16 (or controlled manually) to optimize features such as cell proliferation/differentiation, cell attachment to the fiber scaffold 26, and the composition, density, bite, and texture of the cultured tissue 12. For example, a time frame for proliferation and differentiation of the precursor cells 24 in the first bioreactor 18 (or the transit time in the first bioreactor 18) may be controlled to reach target percentages for differentiation and degree of cell attachment on the fiber scaffold 26. Other controlled parameters may include the degree of twisting of the cell-laden fibers 28 at the second bioreactor 20, the diameter of the yarns 30, the rotation rate of the wheels 80 of the second bioreactor 20, the size and shape of the cultured tissue 12, the packing density of the cultured tissue 12, and the composition of the cultured tissue 12 including the cell types, fiber scaffold composition, and the ratio of muscle-cell laden fibers and fat-cell laden fibers in the cultured tissue product. As noted above, the structural hierarchy and marbling of the cultured tissue construct may be tunable by changing the ratio of muscle cell fibers and fat cell fibers. Warner-Bratzler shear force test may be used to assess the texture and tenderness of the cultured tissue product.

According to the present disclosure, cultured muscle and adipose cells on edible fibers are integrated into tissue assemblies via twisting, weaving or knitting and rolling, stacking, and/or folding to provide versatile outputs that meet target metrics pertaining to properties such as texture, thermal response upon cooking, composition, nutrition, density, alignment, composition, and marbling. This textile engineering-based system is cost-efficient, scalable, and generates cultured meats that mimic whole muscle through the recapitulation of structural hierarchy present in in vivo skeletal muscle. The technique facilitates fabrication of constructs with controlled microstructure, mechanical properties, and cellular distribution which plays an important role in the engineering of structured hierarchical tissues. Furthermore, the utilization of fibril scaffolds enables an effective mass (nutrition)/oxygen transfer in the cell culture system as cell-laden fibers are fully surrounded by culture media, avoiding complications inherent to perfusion systems. By adapting the principles of textile engineering, the technology disclosed herein may enable economic mass production of cultured whole muscle meat.

Figure 6:
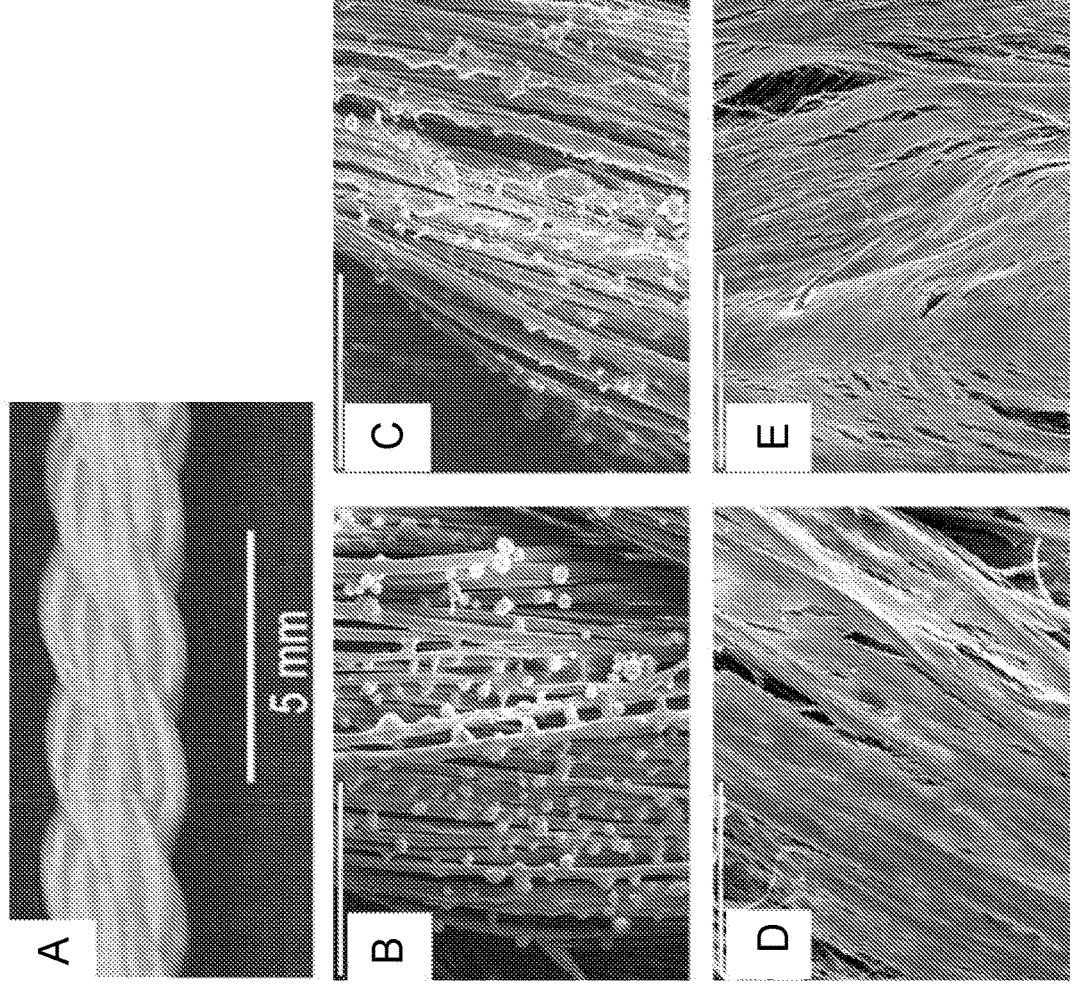
FIG. 6 shows scanning electron microscopy (SEM) images of a silk fiber cord manufactured with a twisting machine, and human mesenchymal stem cells (hMSCs) that attached, spread, and formed confluent cells sheets on the sill fiber cord (scale bar: 100 micrometers (μm)), in accordance with the present disclosure.

To establish proof of concept for at least a portion of the disclosure, reference is made to Altman et al., "Silk-based biomaterials," *Biomaterials,* 2003, 24(3), 401-416, which is incorporated by reference herein in its entirety for all purposes. Briefly, a computer controlled twisting machine having motor-controlled spring-loaded clamps was used to anchor from 2 to 6 fibers or groups of fibers for twisting. A silk cord was manufactured by the twisting equipment. The silk cord contained 5 levels of twisting hierarchy, and 540 individual fibers twisted to the stiffness of human anterior cruciate ligaments (ACL) (see FIG. 6A). Human mesenchymal stem cells (hMSCs) attached, spread, proliferated, and formed confluent cell sheets with extracellular matrix formation on the silk fiber matrices in vitro. FIG. 6B shows initially attached hMSCs on the silk cord shown in FIG. 6A. FIG. 6C shows initial spreading of the hMSCs on the silk cord 1 hour after seeding. FIG. 6D shows hMSCs and extracellular matrix coating the silk cord 7 days post-seeding. FIG. 6E shows thick encapsulation of the silk cord by hMSCs and extracellular matrix 14 days following seeding.

What is claimed is:

1. A system for the production of cultured tissue, comprising:
   a first bioreactor including
      an internal chamber containing culture medium,
      a fiber inlet for feeding a fiber scaffold into the internal chamber, and
      a cell inlet for feeding precursor cells into the internal chamber, wherein the precursor cells proliferate and differentiate on a surface of the fiber scaffold in the culture medium to provide a cell-laden fiber composed of cells attached to the fiber scaffold, and an outlet through which the cell-laden fiber emerges from the first bioreactor, wherein the cell-laden fiber is used in the production of the cultured tissue.

2. The system of claim 1, further comprising a second bioreactor downstream of the first bioreactor and configured to combine and twist the cell-laden fibers emerging from one or more of the first bioreactors to provide a cell-laden yarn.

3. The system of claim 2, wherein the second bioreactor includes wheels attached to each end of the cell-laden fibers which rotate at a rotation rate to twist the cell-laden fibers.

4. The system of claim 2, further comprising a third bioreactor downstream of the second bioreactor and configured to weave or knit the cell-laden yarn into a three-dimensional (3D) structure.

5. The system of claim 2, further comprising a third bioreactor configured to weave or knit the cell-laden yarn from the second bioreactor into a two-dimensional (2D) sheet.

6. The system of claim 5, wherein the third bioreactor is further configured to build the 2D sheet into a three-dimensional (3D) structure.

7. The system of claim 6, wherein the 2D sheet or the 3D structure provides the cultured tissue.

8. The system of claim 7, wherein the cell-laden fiber includes muscle cells, fat cells, or a combination thereof.

9. The system of claim 8, wherein the cell-laden fibers of the cultured tissue include muscle cell-laden fibers, fat cell-laden fibers, or a combination of muscle cell-laden fibers and fat cell-laden fibers.

10. The system of claim 9, wherein the first bioreactor, the second bioreactor, and the third bioreactor are configured to operate automatically and continuously to produce the cultured tissue.

11. The system of claim 10, further comprising one or more computer controllers in communication with the first bioreactor, the second bioreactor, and the third bioreactor for automating the operation of the first bioreactor, the second bioreactor, and the third bioreactor.

12. The system of claim 11, wherein the cells are cultured in a culture media to at least 75% confluence in the first bioreactor.

13. The system of claim 12, wherein a concentration of growth factors in the culture media decreases from a proximal end to a distal end of the first bioreactor.

14. The system of claim 1, wherein the cultured tissue is cultured meat for consumption.

15. The system of claim 1, wherein the cells are engineered to produce vital nutrients.

16. The system of claim 1, wherein the fiber scaffold is edible.

17. The system of claim 11, wherein the one or more computer controllers are configured to control one or more of a time frame for proliferation and differentiation of the precursor cells at the first bioreactor, a degree of twisting of the cell-laden fibers at the second bioreactor, a rotation rate of the wheels of the second bioreactor, a composition of the cultured tissue, a size of the cultured tissue, a cell density of the cultured tissue, a packing density of the cultured tissue, and a ratio of muscle cell-laden fibers and fat cell-laden fibers in the cultured tissue.

18. The system of claim 1, wherein the cells include tetracycline responsive promoters for expression of myogenic or adipogenic genes, and wherein the culture medium includes tetracycline.

19. The system of claim 1, wherein the cultured tissue is composed of muscle cell-laden fibers, fat cell-laden fibers, or a combination of muscle cell-laden fibers and fat cell-laden fibers.

20. The system of claim 1 wherein the fiber scaffold is composed of a material selected from the group consisting of collagen, silk, chitosan, wheat gluten, cellulose, zein, starch, soy protein, fungal mycelia, and combinations thereof.

\* \* \* \* \*